(12) United States Patent
Wu et al.

(10) Patent No.: US 8,420,440 B2
(45) Date of Patent: Apr. 16, 2013

(54) SEMICONDUCTING COMPOSITION

(75) Inventors: Yiliang Wu, Oakville (CA); Anthony James Wigglesworth, Oakville (CA); Ping Liu, Mississauga (CA); Nan-Xing Hu, Oakville (CA)

(73) Assignee: Xerox Corporation, Norwalk, CT (US)

( * ) Notice: Subject to any disclaimer, the term of this patent is extended or adjusted under 35 U.S.C. 154(b) by 239 days.

(21) Appl. No.: 13/024,400

(22) Filed: Feb. 10, 2011

(65) Prior Publication Data

US 2012/0205628 A1 Aug. 16, 2012

(51) Int. Cl.
*H01L 51/56* (2006.01)
*C07D 493/06* (2006.01)

(52) U.S. Cl.
USPC .................. 438/99; 257/40; 549/381

(58) Field of Classification Search .................. 549/381; 438/99; 257/40
See application file for complete search history.

(56) References Cited

U.S. PATENT DOCUMENTS

2009/0289248 A1 11/2009 Kobayashi et al.
2010/0013381 A1 1/2010 Stoessel et al.

OTHER PUBLICATIONS

Kobayashi et al., "Stable peri-Xanthenoxanthene Thin-Film Transistors with Efficient Carrier Injection," Chem. Mater. 2009, 21, 552-556.
Fabbri et al, "Preparation of Enantiomerically Pure 1,1'-Binaphthalene-2,2'-diol and 1,1'-Binaphthalene-2,2'-dithiol," J. Org. Chem. 1993, 58, 1748-1750.
Asari et al, "Charge-Transfer Complexes of PXX (PXX = 6, 12-Dioxaanthanthrene). The Formal Charge and Molecular Geometry," Bull. Chem. Soc. Jpn., 74, 53-58 (2001).
Haryono et al., "Synthesis of a Novel Oligo(p-phenylene) Ladder by Sulfide and Sulfonio Groups," Macromolecules 1999, 32, 3146-3149.
Sirringhaus et al., "Dibenzothienobisbenzothiophene—a novel fused-ring oligomer with high field-effect mobility," J. Mater. Chem. 1999, 9, 2095-2101.
Wigglesworth et al., U.S. Appl. No. 12/977,464, filed Dec. 23, 2010.

Primary Examiner — Bernard Dentz
(74) Attorney, Agent, or Firm — Fay Sharpe LLP

(57) ABSTRACT

A compound of Formula (I):

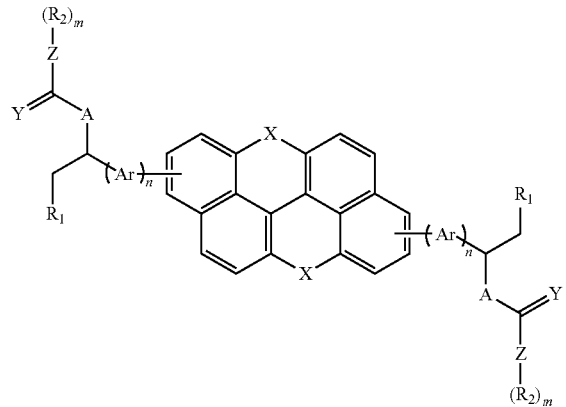

Formula (I)

wherein X, A, Y, Z, $R_1$, $R_2$, Ar, n and m are as described herein. The compound of Formula (I) is useful as part of a semiconducting composition to be deposited upon a surface. When heated, the compound of Formula (I) is converted to a crystalline semiconductor with high mobility.

20 Claims, 2 Drawing Sheets

SEMICONDUCTING COMPOSITION

BACKGROUND

The present disclosure relates to thin-film transistors (TFTs) and/or other electronic devices comprising a semiconducting layer. The semiconducting layer is formed from a semiconductor composition as described herein. When the composition is used in the semiconducting layer of a device, high mobility and excellent stability may be achieved.

TFTs are generally composed of, on a substrate, an electrically conductive gate electrode, source and drain electrodes, an electrically insulating gate dielectric layer which separate the gate electrode from the source and drain electrodes, and a semiconducting layer which is in contact with the gate dielectric layer and bridges the source and drain electrodes. Their performance can be determined by the field effect mobility and the current on/off ratio of the overall transistor. High mobility and high on/off ratio are desired.

Organic thin-film transistors (OTFTs) can be used in applications such as radio frequency identification (RFID) tags and backplane switching circuits for displays, such as signage, readers, and liquid crystal displays, where high switching speeds and/or high density are not essential. They also have attractive mechanical properties such as being physically compact, lightweight, and flexible.

Organic thin-film transistors can be fabricated using low-cost solution-based patterning and deposition techniques, such as spin coating, solution casting, dip coating, stencil/screen printing, flexography, gravure, offset printing, ink jet-printing, micro-contact printing, and the like. To enable the use of these solution-based processes in fabricating thin-film transistor circuits, solution processable materials are therefore required. Small molecule semiconductors may be used to achieve high mobility. However, due to their crystalline nature, small molecule semiconductors also exhibit poor solubility or poor film-forming properties which inhibit the formation of a uniform film. Polymeric semiconductors can be used to form a uniform film. However, polymeric semiconductors typically exhibit lower mobility than small molecule semiconductors.

It would be desirable to develop semiconducting compounds that exhibit high field effect mobility, air stability, and good solubility.

BRIEF DESCRIPTION

The present application discloses, in various embodiments, compounds of Formula (I):

Formula (I)

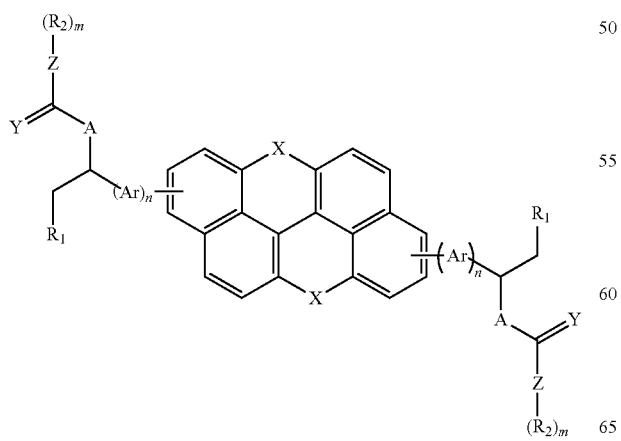

wherein X is O, S, or N—$R_3$; A is O or S; Y is O or S; Z is O, S, N, or C; each Ar is independently aryl, substituted aryl, heteroaryl, or substituted heteroaryl; each n is independently from 0 to about 2; m is the number of $R_2$ sidechains and is an integer from 1 to 3; $R_1$ and $R_3$ are independently hydrogen, alkyl, substituted alkyl, aryl, heteroaryl, substituted aryl, substituted heteroaryl, alkoxy, alkylthio, alkenyl, substituted alkenyl, alkynyl, substituted alkynyl, trialkylsilyl, arylalkyl, alkylaryl, or halogen; and each $R_2$ is independently hydrogen, alkyl, substituted alkyl, aryl, or substituted aryl.

In particular embodiments, X may be oxygen. In others, $R_1$ may be hydrogen or aryl or heteroaryl, particularly phenyl. In particular embodiments, X is oxygen; and $R_1$ is hydrogen, aryl, or heteroaryl.

In specific embodiments, X, A, and Y are O; Z is nitrogen; $R_1$ is hydrogen or phenyl or thienyl; m is 2; and each $R_2$ is independently hydrogen, alkyl or substituted alkyl.

In embodiments, when $R_2$ is an alkyl sidechain, the alkyl sidechain has from 1 to about 10 carbon atoms. In some specific embodiments, $R_3$ is selected from alkyl or arylalkyl.

In some embodiments, X, A, and Y are O; Z is C; $R_1$ is hydrogen or phenyl or thienyl; m is 3; and each $R_2$ sidechain is independently hydrogen, alkyl or substituted alkyl.

In additional specific embodiments, each n is 1; Ar is thienyl or phenyl; $R_2$ is alkyl having from 1 to about 10 carbon atoms, and $R_3$ is alkyl or arylalkyl.

In yet other additional embodiments, X, A, Z, and Y are O; $R_1$ is hydrogen or phenyl or thienyl; m is 1; and $R_2$ is alkyl or substituted alkyl.

The compound may more specifically have the structure of one of Formulas (1) through (16):

Formula (1)

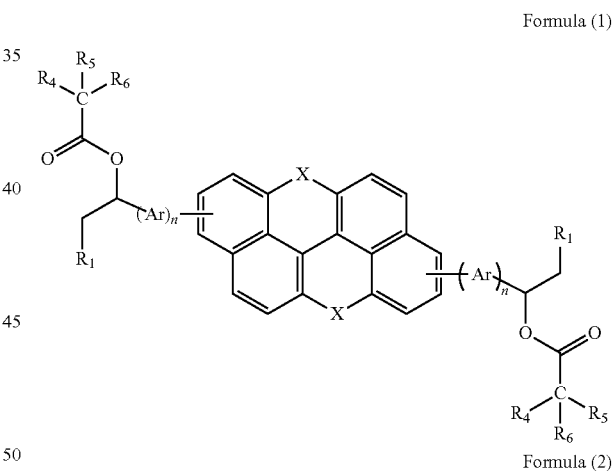

Formula (2)

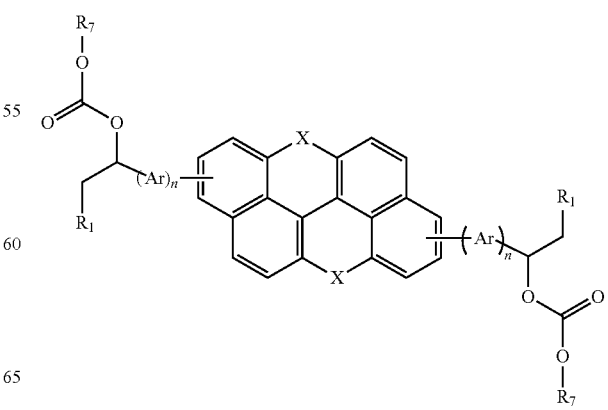

Formula (3)
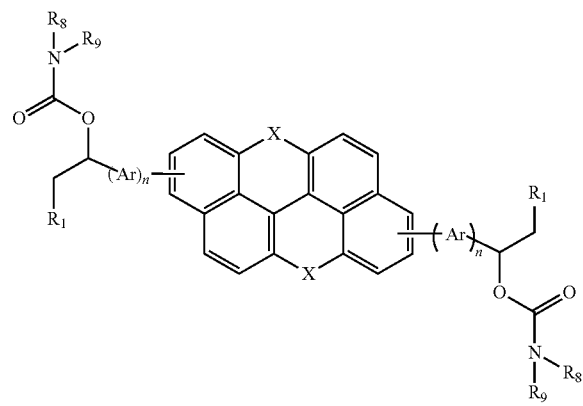
Formula (4)
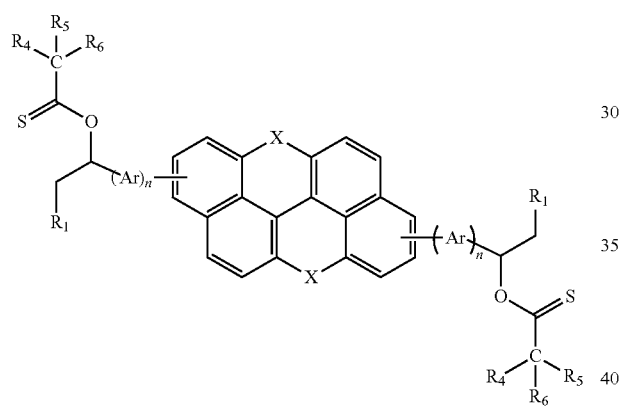
Formula (5)
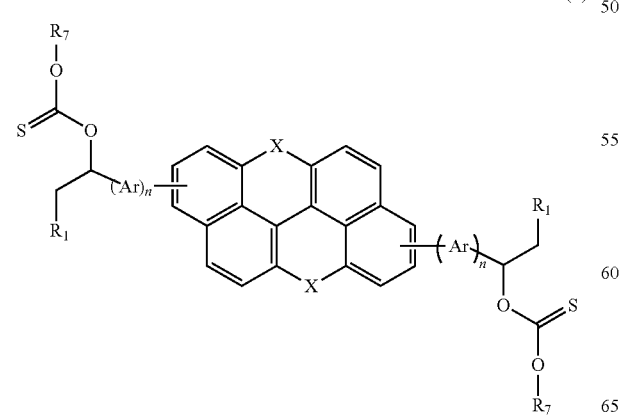
Formula (6)
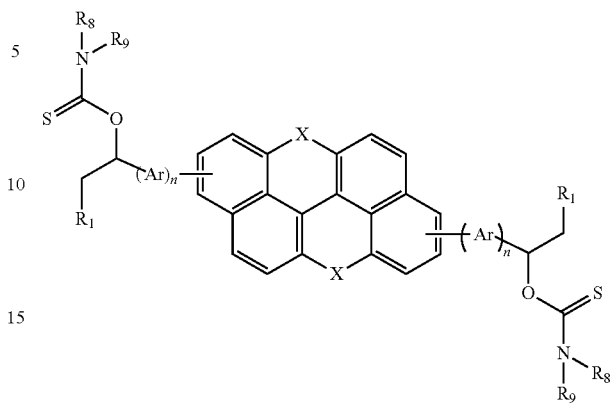
Formula (7)
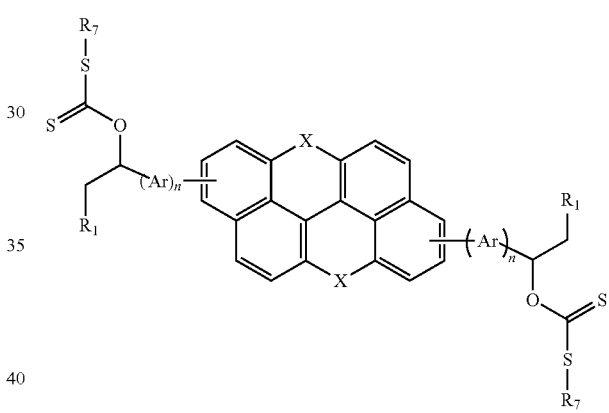
Formula (8)
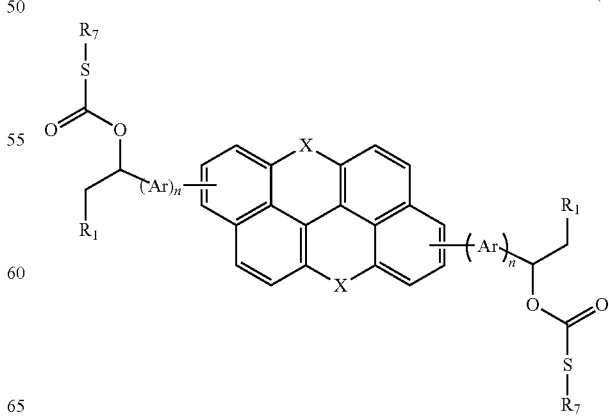

Formula (9)
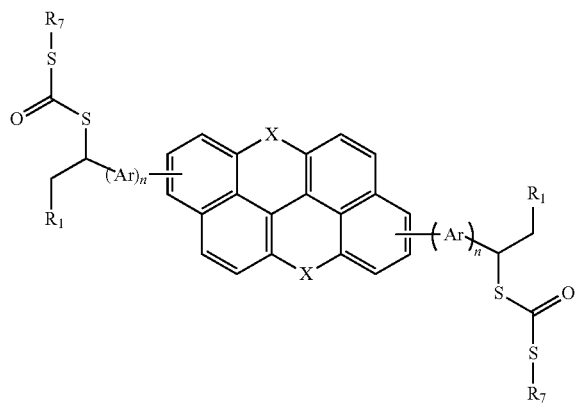
Formula (12)
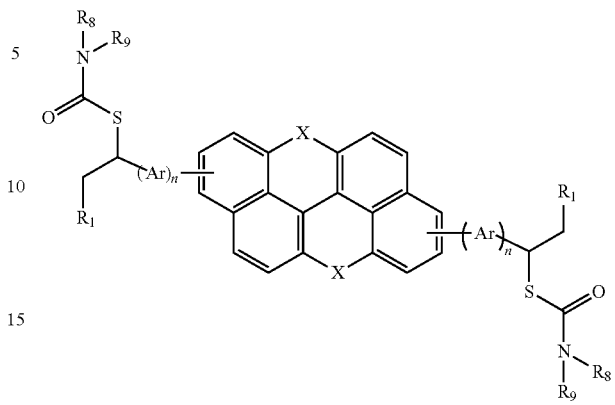
Formula (10)
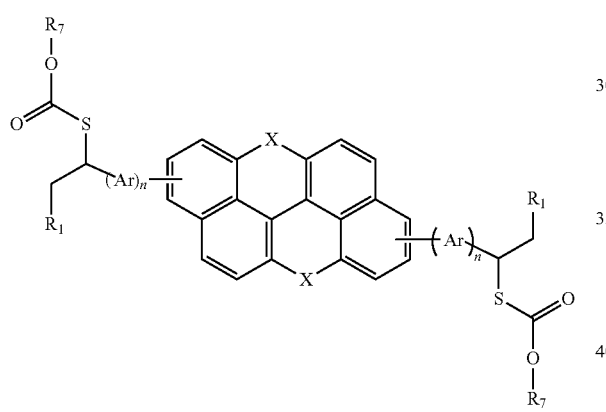
(Formula 13)
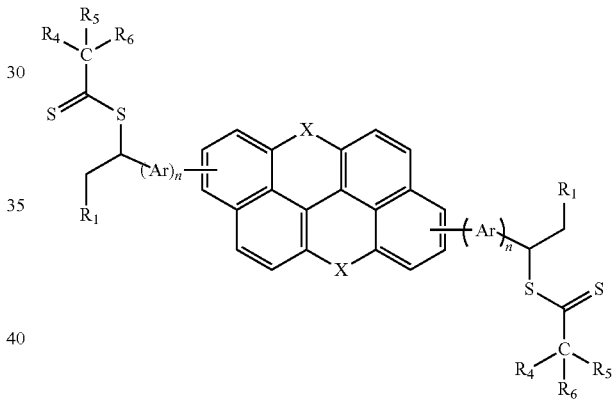
Formula (11)
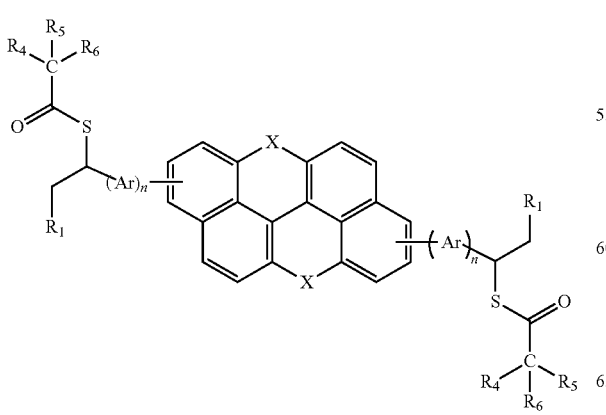
(Formula 14)
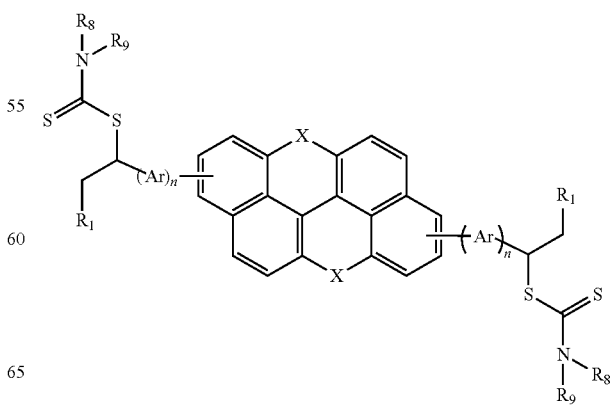

-continued (Formula 15)

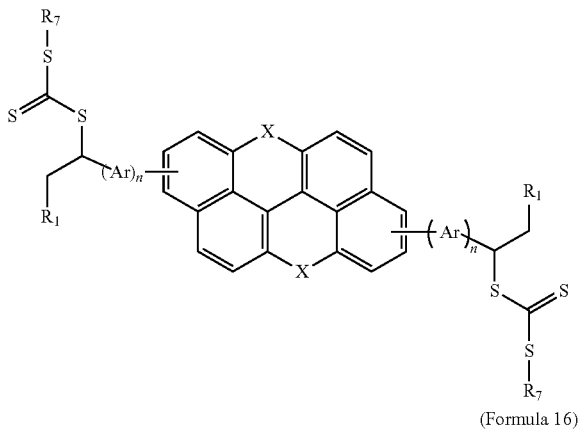

(Formula 16)

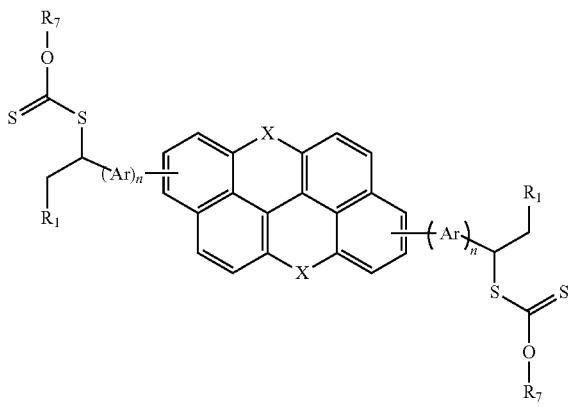

wherein $R_4$, $R_5$, $R_6$, $R_8$, and $R_9$ are independently hydrogen, alkyl, substituted alkyl, aryl, or substituted aryl; and $R_7$ is alkyl, substituted alkyl, aryl, or substituted aryl.

Also disclosed is a process of fabricating a semiconducting layer of an electronic device, such as a thin-film transistor. The process includes liquid depositing a semiconductor composition onto a surface and heating the semiconductor composition to form a semiconducting layer. The semiconductor composition comprises a compound of Formula (I):

Formula (I)

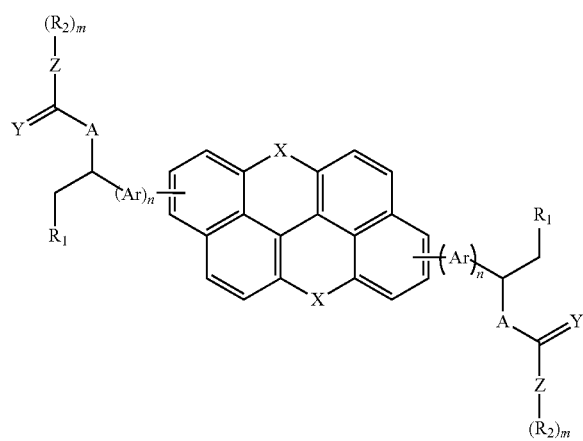

wherein X is O, S, or N—$R_3$; A is O or S; Y is O or S; Z is O, S, N, or C; each Ar is independently aryl, substituted aryl, heteroaryl, or substituted heteroaryl; each n is independently from 0 to about 2; m is the number of $R_2$ sidechains and is an integer from 1 to 3; $R_1$ and $R_3$ are independently hydrogen, alkyl, substituted alkyl, aryl, heteroaryl, substituted aryl, substituted heteroaryl, alkoxy, alkylthio, alkenyl, substituted alkenyl, alkynyl, substituted alkynyl, trialkylsilyl, arylalkyl, alkylaryl, or halogen; and each $R_2$ is independently hydrogen, alkyl, substituted alkyl, aryl, or substituted aryl.

The semiconductor composition may be heated to a temperature of from about 100° C. to about 250° C.

$R_1$ may be hydrogen or aryl or heteroaryl. In some embodiments, $R_1$ is phenyl or thienyl.

In some embodiments, X is oxygen, and $R_1$ is hydrogen or aryl. The aryl may be phenyl.

In some embodiments, X, A, Y and Z are O; n is 0; $R_1$ is hydrogen or aryl; m is 1; and $R_2$ is hydrogen, alkyl or substituted alkyl.

In other embodiments, X is O; $R_1$ is hydrogen or aryl; each n is 1; Ar is thienyl or phenyl; and each $R_2$ is hydrogen or alkyl having from 1 to about 10 carbon atoms.

In other embodiments, X, A, and Y are O; Z is carbon; $R_1$ is hydrogen or aryl; m is 3; and each $R_2$ is independently hydrogen, alkyl or substituted alkyl.

In other embodiments, X, A, Y and Z are O; each n is 0; $R_1$ is hydrogen or aryl; m is 1; and $R_2$ is alkyl or substituted alkyl.

In particular embodiments, the compound of Formula (I) is an amorphous compound, and the semiconductor layer is predominantly crystalline.

Disclosed in other embodiments is an electronic device comprising a semiconducting layer. The semiconducting layer is formed by liquid depositing a semiconductor composition onto a surface and heating the semiconductor composition to form the semiconducting layer. The semiconductor composition comprises a compound of Formula (I):

Formula (I)

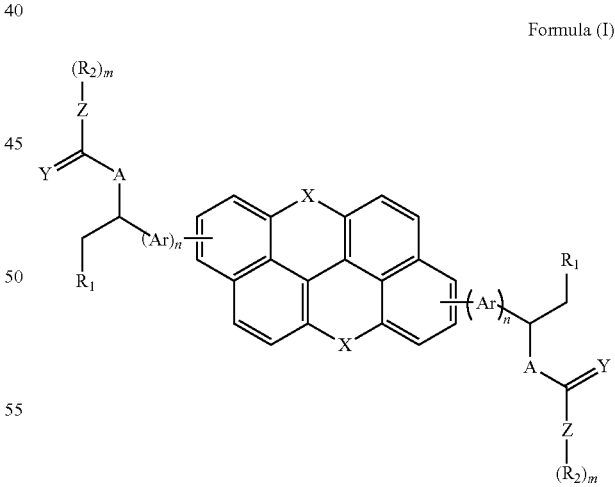

wherein X is O, S, or N—$R_3$; A is O or S; Y is O or S; Z is O, S, N, or C; each Ar is independently aryl, substituted aryl, heteroaryl, or substituted heteroaryl; each n is independently from 0 to about 2; m is the number of $R_2$ sidechains and is an integer from 1 to 3; $R_1$ and $R_3$ are independently hydrogen, alkyl, substituted alkyl, aryl, heteroaryl, substituted aryl, substituted heteroaryl, alkoxy, alkylthio, alkenyl, substituted alkenyl, alkynyl, substituted alkynyl, trialkylsilyl, arylalkyl, alkylaryl, or halogen; and each $R_2$ is independently hydrogen, alkyl, substituted alkyl, aryl, or substituted aryl.

$R_1$ may be hydrogen or aryl or heteroaryl. In embodiments, the aryl is phenyl. $R_2$ may be alkyl having from 1 to about 10 carbon atoms. In some other embodiments, each n is 0. The semiconductor layer may be predominantly crystalline.

The semiconductor layer may comprise a compound of Formula (II) and a residual amount of the compound of Formula (I):

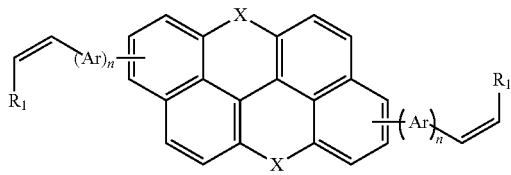

Formula (II)

wherein X is O, S, or N—$R_3$; each Ar is independently aryl, substituted aryl, heteroaryl, or substituted heteroaryl; each n is independently from 0 to about 2; and $R_1$ is hydrogen, alkyl, substituted alkyl, aryl, heteroaryl, substituted aryl, substituted heteroaryl, alkoxy, alkylthio, alkenyl, substituted alkenyl, alkynyl, substituted alkynyl, trialkylsilyl, arylalkyl, alkylaryl, or halogen.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
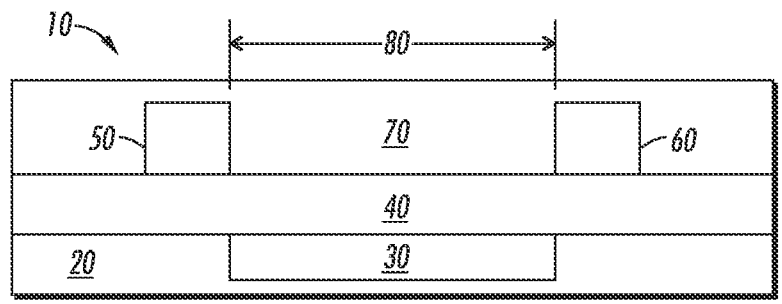
FIG. 1 is a diagram of a first embodiment of a TFT according to the present disclosure.

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range of "from about 2 to about 10" also discloses the range "from 2 to 10."

The term "comprising" is used herein as requiring the presence of the named component and allowing the presence of other components. The term "comprising" should be construed to include the term "consisting of", which allows the presence of only the named component, along with any impurities that might result from the manufacture of the named component.

The present disclosure relates to compounds of Formula (I) as disclosed herein. These compounds can be used in semiconductor compositions that are useful for forming semiconducting layers in electronic devices, such as thin-film transistors (TFTs). Also disclosed are processes for forming the semiconducting layer of an electronic device from the compounds of Formula (I).

FIG. 1 illustrates a bottom-gate bottom-contact TFT configuration according to the present disclosure. The TFT 10 comprises a substrate 20 in contact with the gate electrode 30 and a gate dielectric layer 40. The gate electrode 30 is depicted here in a depression within the substrate 20, but the gate electrode could also be located atop the substrate. It is important that the gate dielectric layer 40 separates the gate electrode 30 from the source electrode 50, drain electrode 60, and the semiconducting layer 70. The semiconducting layer 70 runs over and between the source and drain electrodes 50 and 60. The semiconductor has a channel length 80 between the source and drain electrodes 50 and 60.

Figure 2:
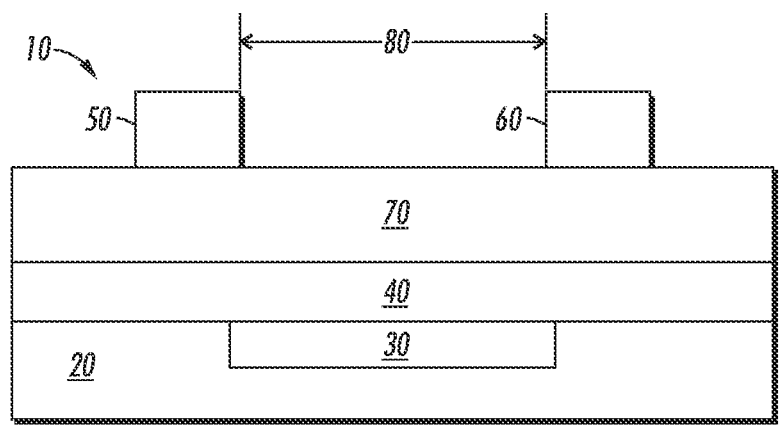
FIG. 2 is a diagram of a second embodiment of a TFT according to the present disclosure.

FIG. 2 illustrates another bottom-gate top-contact TFT configuration according to the present disclosure. The TFT 10 comprises a substrate 20 in contact with the gate electrode 30 and a gate dielectric layer 40. The semiconducting layer 70 is placed on top of the gate dielectric layer 40 and separates it from the source and drain electrodes 50 and 60.

Figure 3:
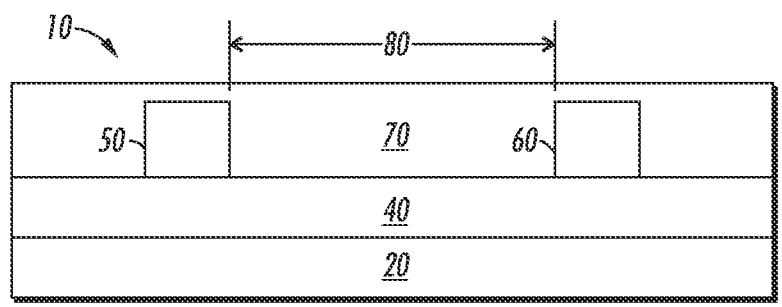
FIG. 3 is a diagram of a third embodiment of a TFT according to the present disclosure.

FIG. 3 illustrates a bottom-gate bottom-contact TFT configuration according to the present disclosure. The TFT 10 comprises a substrate 20 which also acts as the gate electrode and is in contact with a gate dielectric layer 40. The source electrode 50, drain electrode 60, and semiconducting layer 70 are located atop the gate dielectric layer 40.

Figure 4:
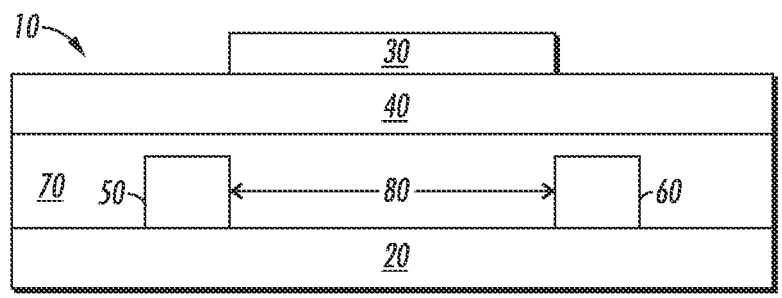
FIG. 4 is a diagram of a fourth embodiment of a TFT according to the present disclosure.

FIG. 4 illustrates a top-gate top-contact TFT configuration according to the present disclosure. The TFT 10 comprises a substrate 20 in contact with the source electrode 50, drain electrode 60, and the semiconducting layer 70. The semiconducting layer 70 runs over and between the source and drain electrodes 50 and 60. The gate dielectric layer 40 is on top of the semiconducting layer 70. The gate electrode 30 is on top of the gate dielectric layer 40 and does not contact the semiconducting layer 70.

The compounds of the present disclosure have two bulky substituents, as seen in the structure of Formula (I):

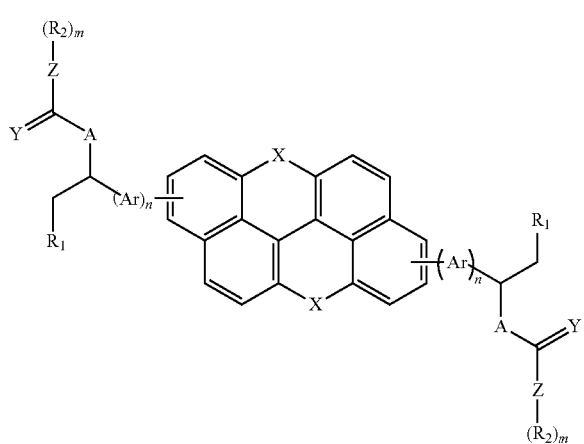

Formula (I)

wherein X is O, S, or N—R$_3$; A is O or S; Y is O or S; Z is O, S, N, or C; each Ar is independently aryl, substituted aryl, heteroaryl, or substituted heteroaryl; each n is independently from 0 to about 2; m is the number of R$_2$ sidechains and is an integer from 1 to 3; R$_1$ and R$_3$ are independently hydrogen, alkyl, substituted alkyl, aryl, heteroaryl, substituted aryl, substituted heteroaryl, alkoxy, alkylthio, alkenyl, substituted alkenyl, alkynyl, substituted alkynyl, trialkylsilyl, arylalkyl, alkylaryl, or halogen; and each R$_2$ is independently hydrogen, alkyl, substituted alkyl, aryl, or substituted aryl.

The fused rings of the compound may be referred to as the core of the small molecule semiconductor. When X is O, the core is referred to as a xanthenoxanthene core. When X is S, the core is referred to as a thioxanthenothioxanthene core. When X is N—R$_3$, the core is referred to as an acridinoacridine core. A numbered version of the core is illustrated in Formula (I-A):

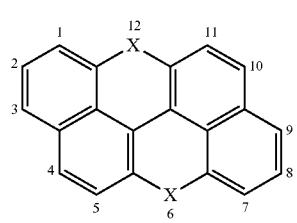

Formula (I-A)

One of the bulky substituents,

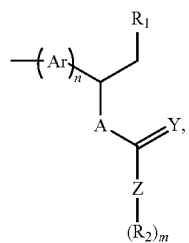

is located on the core at any position from 1 to 5 on one side. The other bulky substituent is located on the core at any position from 7 to 11 on the other side. The two substituents do not have to be placed on symmetrical carbon atoms (i.e. 2 and 8, or 3 and 9). However, in some particular embodiments, the two substituents are placed on symmetrical carbon atoms.

The term "alkyl" refers to a radical composed entirely of carbon atoms and hydrogen atoms which is fully saturated. The alkyl radical may be linear, branched, or cyclic. The alkyl radical may be bonded to one or two different non-hydrogen atoms. For example, the formulas —CH$_2$—CH$_3$ and —CH$_2$—CH$_2$— should both be considered alkyl.

The term "alkenyl" refers to a radical composed entirely of carbon atoms and hydrogen atoms which contains at least one carbon-carbon double bond that is not part of an aryl or heteroaryl structure. The alkenyl radical may be linear, branched, or cyclic. The alkenyl radical may be bonded to one or two different non-hydrogen atoms.

The term "alkynyl" refers to a radical composed entirely of carbon atoms and hydrogen atoms which contains at least one carbon-carbon triple bond. The alkynyl radical may be bonded to one or two different non-hydrogen atoms.

The term "aryl" refers to an aromatic radical composed entirely of carbon atoms and hydrogen atoms. When aryl is described in connection with a numerical range of carbon atoms, it should not be construed as including substituted aromatic radicals. For example, the phrase "aryl containing from 6 to 10 carbon atoms" should be construed as referring to a phenyl group (6 carbon atoms) or a naphthyl group (10 carbon atoms) only, and should not be construed as including a methylphenyl group (7 carbon atoms). The aryl radical may be bonded to one or two different non-hydrogen atoms. For example, the radicals —C$_6$H$_5$ and —C$_6$H$_4$— could both be referred to as phenyl and should both be considered aryl radicals.

The term "heteroaryl" refers to a cyclic radical composed of carbon atoms, hydrogen atoms, and a heteroatom within a ring of the radical, the cyclic radical being aromatic. The heteroatom may be nitrogen, sulfur, or oxygen. Exemplary heteroaryl groups include thienyl, pyridinyl, and quinolinyl. When heteroaryl is described in connection with a numerical range of carbon atoms, it should not be construed as including substituted heteroaromatic radicals. The heteroaryl radical may be bonded to one or two different non-hydrogen atoms. For example, the radicals —C$_4$H$_3$S and —C$_4$H$_2$S— could both be referred to as thienyl and should both be considered heteroaryl radicals.

The term "alkoxy" refers to an alkyl radical which is attached to an oxygen atom, e.g. —O—C$_n$H$_{2n+1}$. The oxygen atom attaches to the core of the compound.

The term "alkylthio" refers to an alkyl radical which is attached to a sulfur atom, e.g. —S—C$_n$H$_{2n+1}$. The sulfur atom attaches to the core of the compound.

The term "trialkylsilyl" refers to a radical composed of a tetravalent silicon atom having three alkyl radicals attached to the silicon atom, i.e. —Si(R)$_3$. The three alkyl radicals may be the same or different. The silicon atom attaches to the core of the compound.

The term "arylalkyl" refers to an aromatic radical which is connected to an alkyl radical. The alkyl radical attaches to the core of the compound. The arylalkyl radical can also be substituted. An exemplary arylalkyl radical is benzyl (—CH$_2$—C$_6$H$_5$). It should be noted that an arylalkyl radical is a subset of the set of substituted alkyl radicals.

The term "alkylaryl" refers to an alkyl radical which is connected to an aromatic radical. The aromatic radical attaches to the core of the compound. The alkylaryl radical can also be substituted. An exemplary alkylaryl radical is methylphenyl (—$C_6H_4$—$CH_3$). It should be noted that an alkylaryl radical is a subset of the set of substituted aryl radicals.

The term "substituted" refers to at least one hydrogen atom on the named radical being substituted with another functional group, such as halogen, —CN, —$NO_2$, —COOH, and —$SO_3H$. An exemplary substituted alkyl group is a perhaloalkyl group, wherein one or more hydrogen atoms in an alkyl group are replaced with halogen atoms, such as fluorine, chlorine, iodine, and bromine. Besides the aforementioned functional groups, an alkyl, alkenyl, or alkynyl group may also be substituted with an aryl or heteroaryl group. An exemplary substituted alkenyl group is phenylethenyl (—CH=CH—$C_6H_5$). An exemplary substituted alkynyl group is phenylethynyl (—C≡C—$C_6H_5$). An aryl or heteroaryl group may also be substituted with alkyl or alkoxy. Exemplary substituted aryl groups include methylphenyl and methoxyphenyl. Exemplary substituted heteroaryl groups include 3-methylthienyl.

Generally, the alkyl and alkoxy groups each independently contain from 1 to 30 carbon atoms. The alkyl and alkoxy groups may also contain from 1 to about 10 carbon atoms. Similarly, the aryl group may contain from 6 to 30 carbon atoms. Heteroaryl groups may contain from 5 to 25 carbon atoms.

It should be noted that the value of m depends on the Z atom. When Z is oxygen or sulfur, m is 1. When Z is nitrogen, m is 2. When Z is carbon, m is 3. The notation of Formula (I) should not be construed such that, for example, when Z is carbon, m can be 1 or 2.

In some embodiments, X is O; and $R_1$ is hydrogen, aryl, or heteroaryl. In other particular embodiments, each $R_2$ is selected from hydrogen, alkyl, or substituted alkyl. When $R_1$-$R_3$ are alkyl, the alkyl may have from 1 to about 10 carbon atoms. When $R_1$ is aryl, the aryl may be phenyl. When $R_1$ is heteroaryl, the heteroaryl may be thienyl.

In some embodiments, n is 0. In other embodiments, n is 1. Each Ar moiety may be independently selected from the group consisting of the following structures:

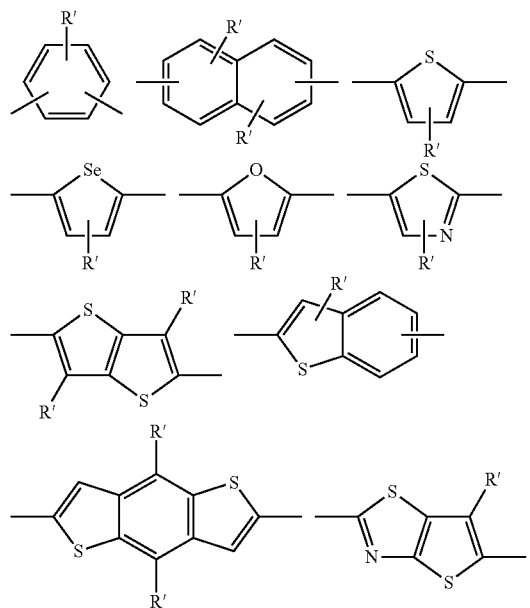

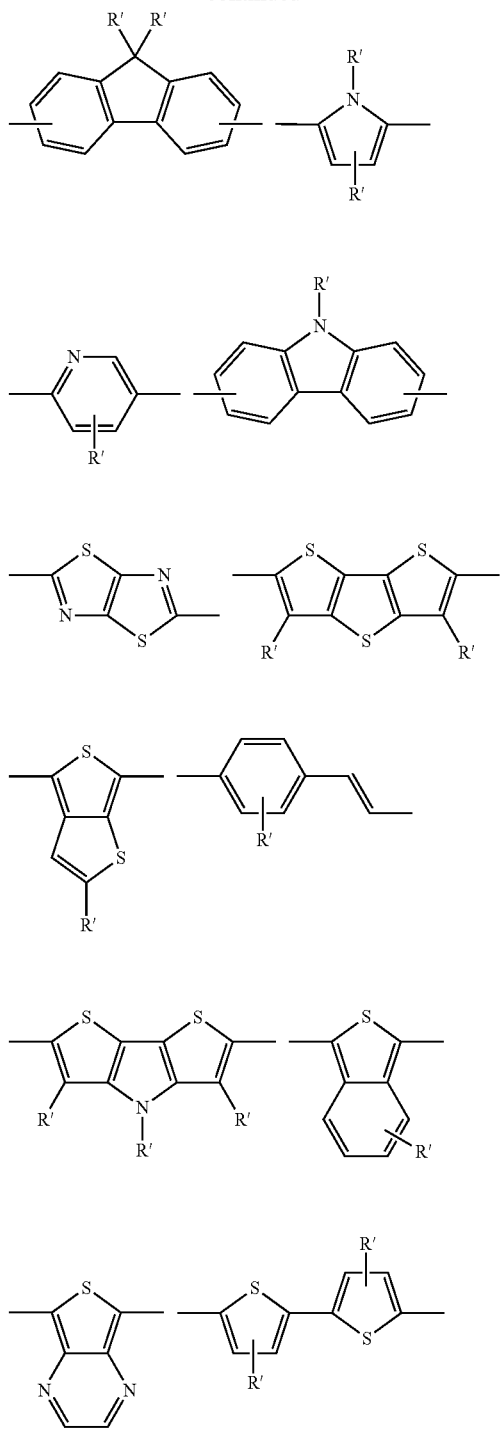

where R' is independently selected from hydrogen, alkyl containing from 1 to about 16 carbon atoms, substituted alkyl, aryl, substituted aryl, alkoxy or substituted alkoxy, a heteroatom-containing group, halogen, —CN, or —$NO_2$.

In specific embodiments, each Ar is phenyl or thienyl.

The compound of Formula (I) may more specifically have one of the structures shown here as Formulas (1) to (16):

Formula (1)
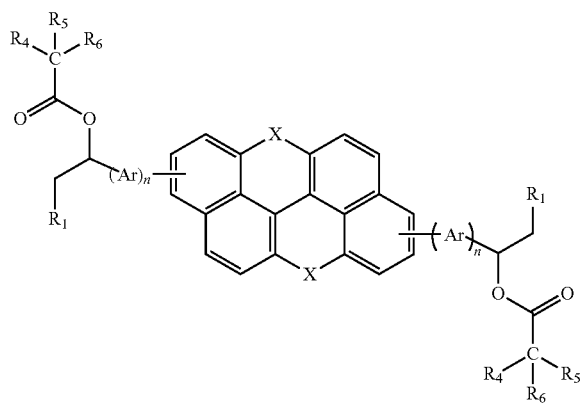
Formula (2)
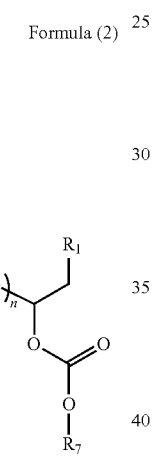
Formula (3)
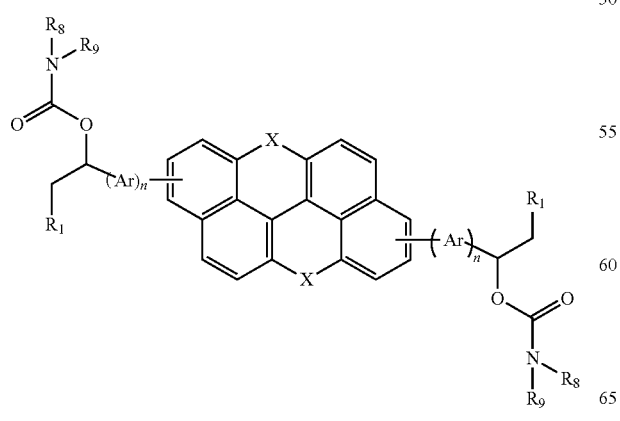
Formula (4)
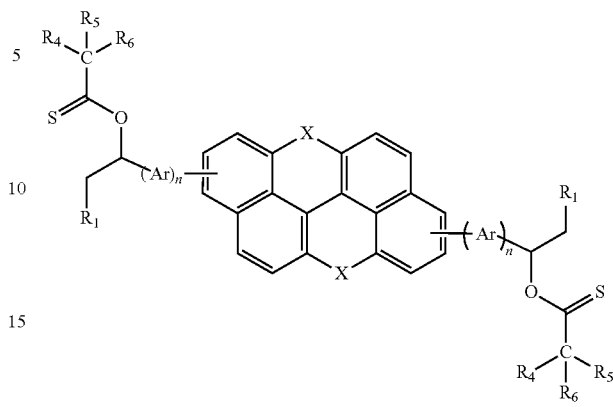
Formula (5)
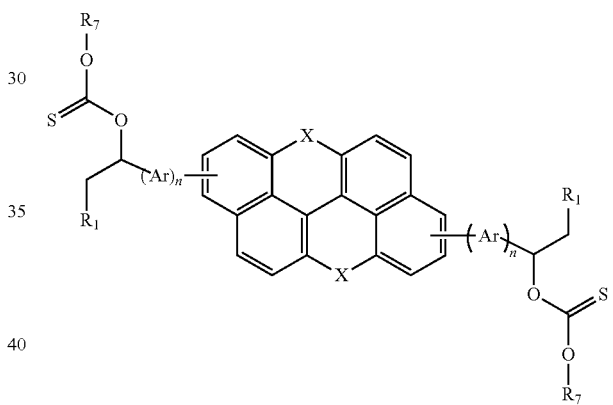
Formula (6)
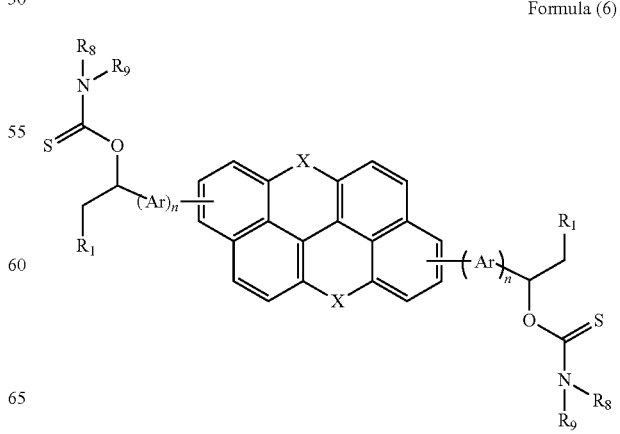

Formula (7)
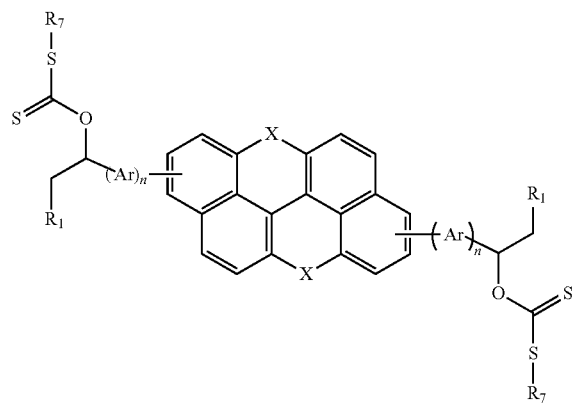
Formula (8)
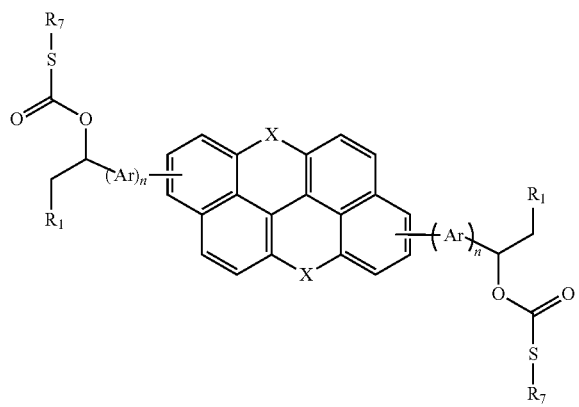
Formula (9)
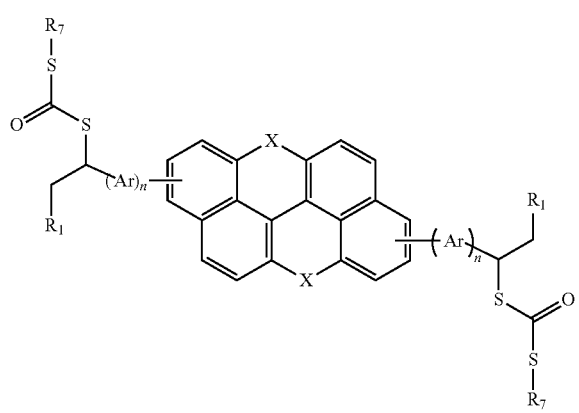
Formula (10)
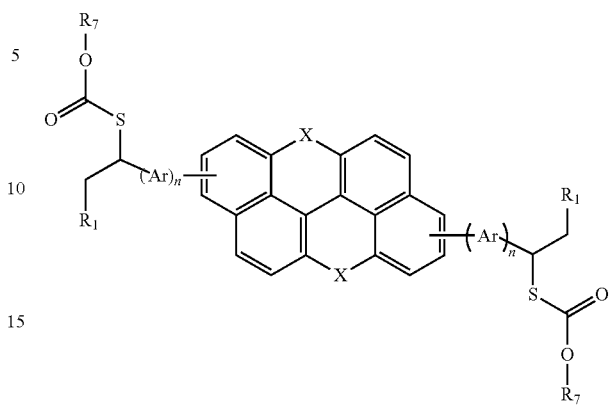
Formula (11)
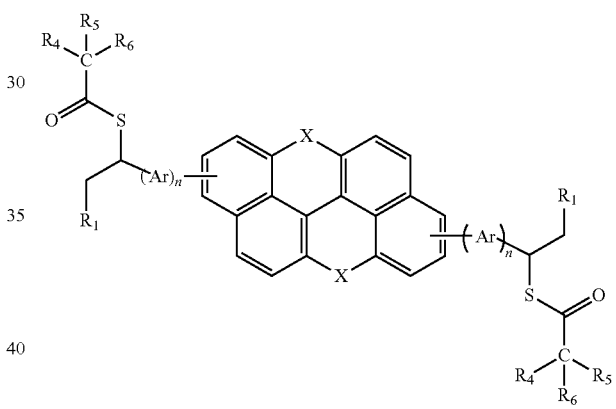
Formula (12)
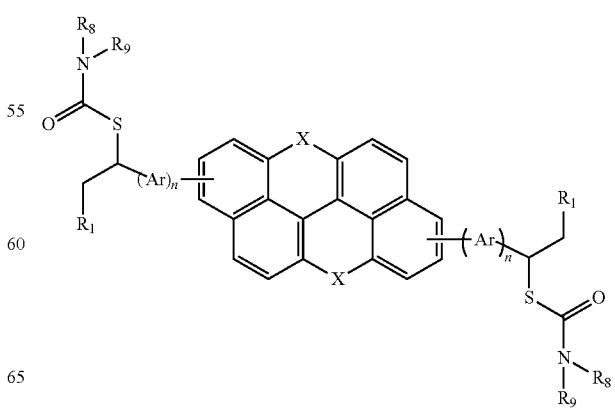

(Formula 13)

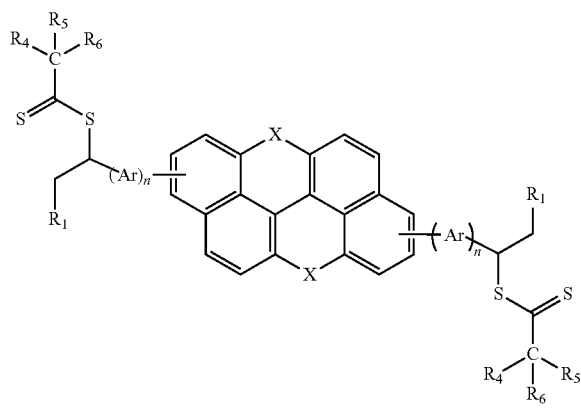

(Formula 14)

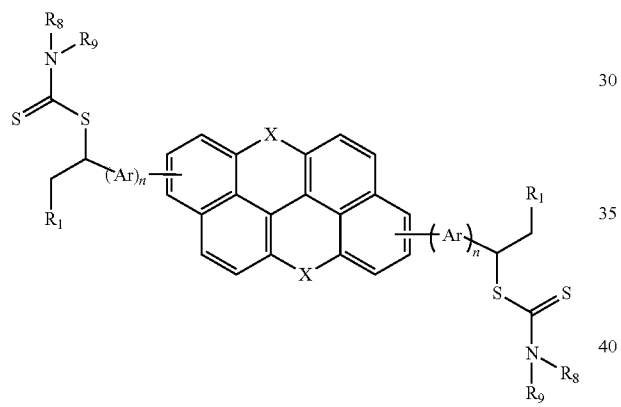

(Formula 15)

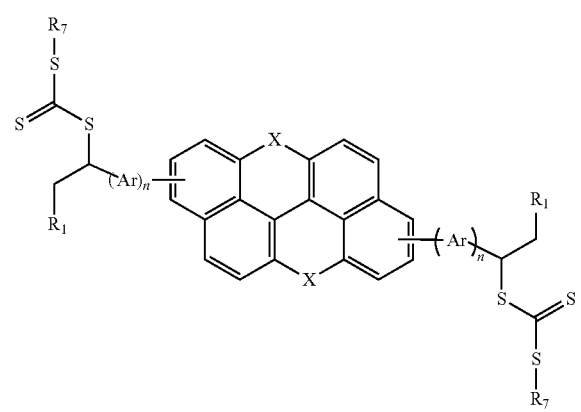

(Formula 16)

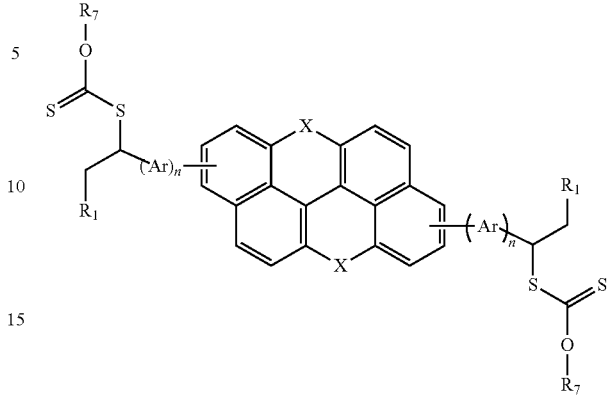

wherein $R_4$, $R_5$, $R_6$, $R_8$, and $R_9$ are independently hydrogen, alkyl, substituted alkyl, aryl, or substituted aryl; and $R_7$ is alkyl, substituted alkyl, aryl, or substituted aryl.

In specific embodiments, X, A, and Y are O; Z is nitrogen; $R_1$ is hydrogen or phenyl or thienyl; m is 2; and each $R_2$ is independently hydrogen, alkyl, or substituted alkyl. This corresponds to Formula (3), where $R_8$ and $R_9$ are the two $R_2$ sidechains.

In other embodiments, $R_2$ is alkyl having from 1 to about 10 carbon atoms, and $R_3$ is alkyl or arylalkyl. In such embodiments, X is N—$R_3$.

In other embodiments, X, A, and V are 0; Z is C; $R_1$ is hydrogen or phenyl; m is 3, $R_2$ is independently hydrogen, alkyl or substituted alkyl. In specific embodiments, n is 0; m is 3; one $R_2$ sidechain is hydrogen, and two of the $R_2$ sidechains are independently alkyl or substituted alkyl. This compound can correspond to Formula (1) or to Formula (1-a) as shown below:

Formula (1-a)

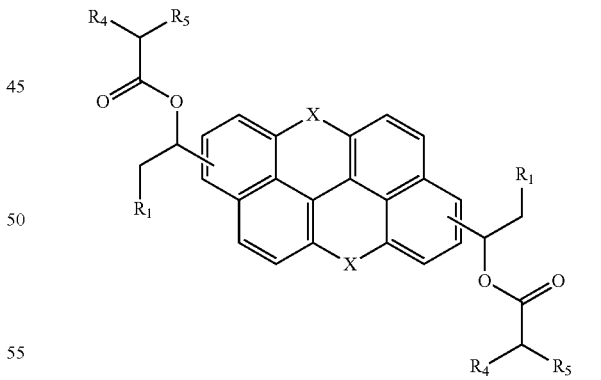

As seen here, each Z atom is carbon, with one sidechain ($R_6$) being hydrogen, and two sidechains ($R_4$ and $R_5$) which are independently alkyl or substituted alkyl.

In embodiments, the compound of Formula (I) is an amorphous compound. Whether the compound is amorphous can be determined using methods known in the art. For example, using the DSC method, the absence of a melting peak is characteristic of an amorphous compound. Similarly, using an X-ray diffraction method, no diffraction peaks can be observed in an amorphous compound. The amorphous nature of the compounds of the present disclosure offer significant advantages for forming a uniform film upon liquid deposition such as spin coating, dip coating, and inkjet printing.

When heated, the compound of Formula (I) can be converted to a small molecule semiconductor of Formula (II) by removal of the bulky solubilizing groups, as illustrated below:

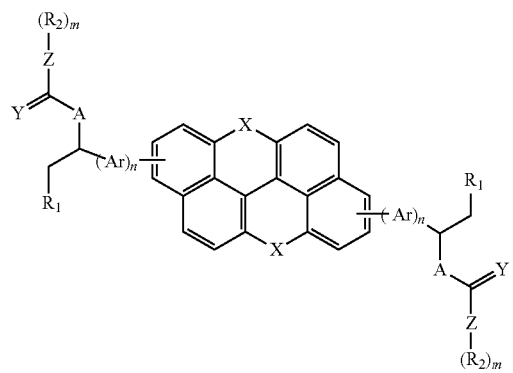

Formula (I)

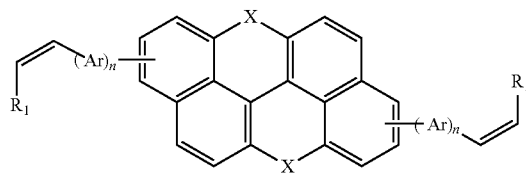

Formula (II)

The small molecule semiconductor of Formula (II) may also be formed from other synthetic routes. However, when the small molecule semiconductor of Formula (II) itself is deposited on a substrate or a dielectric layer, uniform film forming may be difficult to achieve due to the crystallinity of such small molecules. Depositing the compound of Formula (I) improves film uniformity because the compound of Formula (I) includes thermally removable solubilizing groups, which make the compound of Formula (I) more amorphous and soluble. However, the final small molecule compound of Formula (II) is highly crystalline and expected to exhibit high mobility. In short, when the compound of Formula (I) is used as disclosed herein, amorphous film-forming properties and highly crystalline semiconductor properties can be combined to yield a solution processable semiconducting layer which exhibits excellent mobility. Put another way, the amorphous characteristics of the small molecule semiconductor compound of Formula (I) enable coating a uniform film; when thermally converted into a compound of Formula (II), the crystalline characteristics of the small molecule semiconductor compound of Formula (II) enable high field effect mobility.

The compound of Formula (I) may be synthesized via the following three-step procedure when X is oxygen. First, a xanthenoxanthene core XX structure undergoes a Friedel-Crafts reduction as illustrated below:

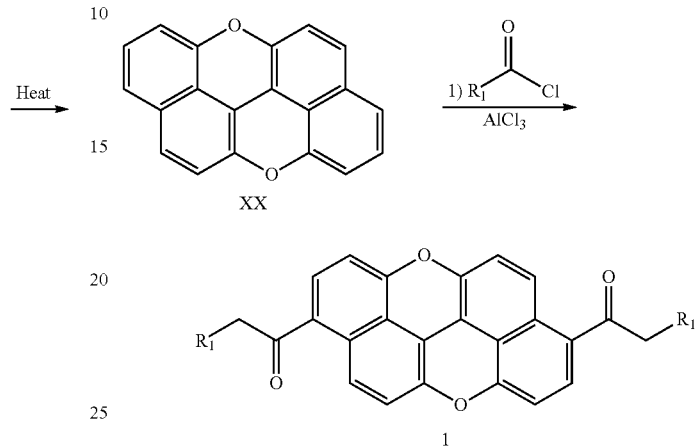

Next, the carbonyl of compound 1 can be reduced using, for example, lithium aluminum hydride (LAH) as depicted below:

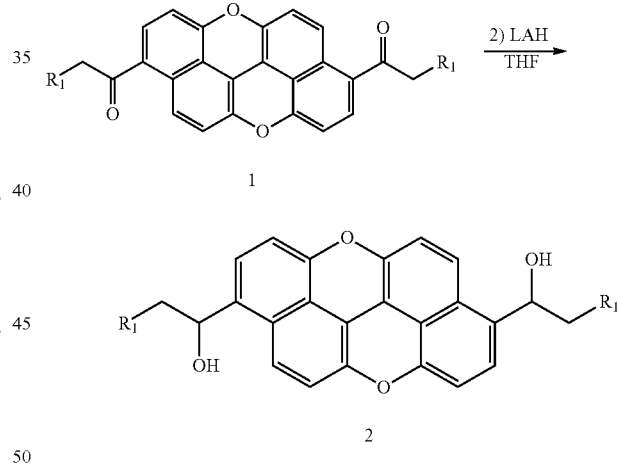

Finally, compound 2 can be esterified, for example, with 2-butyloctanoyl chloride to form the small molecule semiconductor 3 of Formula (1). This reaction is shown below:

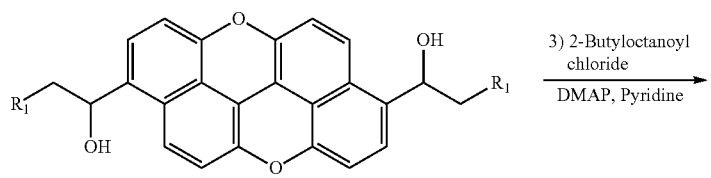

-continued

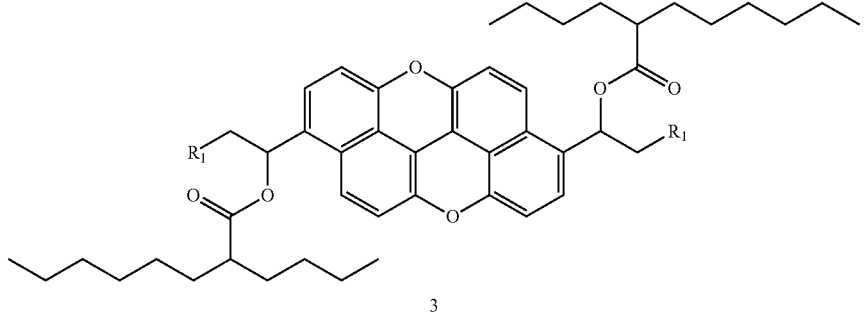

3

The xanthenoxanthene core XX is reproduced below with the substituent positions numbered:

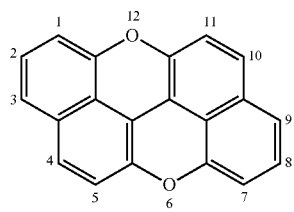

XX

The bulky substituents will generally be attached at either the 1- and 7-positions, the 2- and 8-positions, or the 3- and 9-positions.

The above-described small molecule semiconductors may be used to fabricate semiconducting layers in electronic devices. In particular, the small molecule semiconductors may be used in the fabrication of thin-film transistors.

Processes for fabricating electronic devices are also disclosed. Generally, a semiconductor composition is deposited onto a surface and then heated to form a semiconducting layer. The surface may be the surface of a substrate or a dielectric layer. The semiconductor composition comprises a compound of Formula (I):

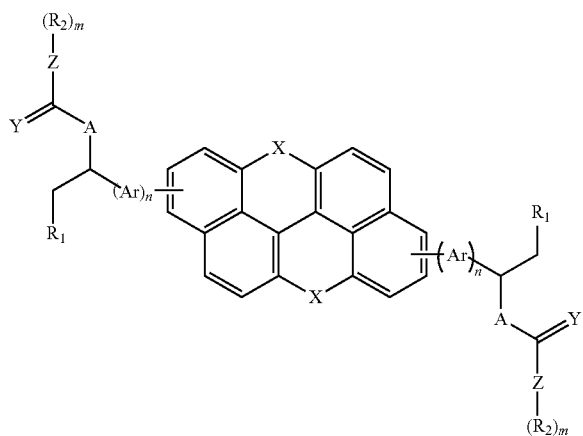

Formula (I)

wherein X is O, S, or N—$R_3$; A is O or S; Y is O or S; Z is O, S, N, or C; each Ar is independently aryl, substituted aryl, heteroaryl, or substituted heteroaryl; each n is independently from 0 to about 2; m is the number of $R_2$ sidechains and is an integer from 1 to 3; $R_1$ and $R_3$ are independently hydrogen, alkyl, substituted alkyl, aryl, heteroaryl, substituted aryl, substituted heteroaryl, alkoxy, alkylthio, alkenyl, substituted alkenyl, alkynyl, substituted alkynyl, trialkylsilyl, arylalkyl, alkylaryl, or halogen; and each $R_2$ is independently hydrogen, alkyl, substituted alkyl, aryl, or substituted aryl.

The semiconductor composition may be heated to a temperature of from about 100° C. to about 300° C., including from about 100° C. to about 250° C., or from about 10° C. to about 20° C. The heating may occur from about 30 seconds to about 2 hours, including from about 1 minute to about 60 minutes, or from about 5 minutes to about 30 minutes.

When heated, the compound of Formula (I) can be converted in-situ in the electronic device into the compound of Formula (II). In embodiments, the conversion rate is at least 85%, including from about 90% to 100%, from about 95% to about 99.8%, measured by molar percentage (mole %). In some embodiments, there is no residual amount of the compound of Formula (I). In other embodiments, there is a residual amount of the compound of Formula (I). The presence of a very small amount of compound of Formula (I) has no or little effect on the electrical performance of the electric devices. After heating, in embodiments, the residual amount of the compound of Formula (I) in the semiconductor layer is from about 10 mole % to about 0.001 mole %, or from about 5 mole % to about 0.01 mole %, or from about 0.5 mole % to about 0.01 mole %.

A semiconductor composition may be formed that comprises the compound of Formula (I) and a polymer binder. It should be noted that the polymer binder is optional. The use of a polymer binder may further enhance the film-forming property of the semiconductor composition. The polymer binder can be considered as forming a matrix within which the compound of Formula (I) is dispersed.

Any suitable polymer can be used as the polymer binder for the semiconductor composition. In some embodiments, the polymer is an amorphous polymer. The amorphous polymer may have a glass transition temperature less than the decomposition temperature (conversion temperature) of the compound of Formula (I). In other embodiments, the amorphous polymer has a glass transition temperature greater than the conversion temperature of compound of Formula (I). In embodiments, the polymer has a dielectric constant less than 4.5, preferably less than 3.5, including less than 3.0, as measured at 60 Hz at room temperature. In embodiments, the polymer is selected from polymers containing only C, H, F, Cl, or N atoms. In some embodiments, the polymer is a low polarity polymer, such as a hydrocarbon polymer or a fluorocarbon polymer without any polar groups. For example, polystyrene is an amorphous polymer and has a dielectric constant about 2.6. A list of other low polarity polymers includes but is not limited to the following: fluoropolyarylether, poly(p-xylylene), poly(vinyl toluene), poly(α-methyl styrene), poly(a-vinylnaphthalene), polyethylene, polypropylene, polyisoprene, poly(tetrafluoroethylene), poly (chlorotrifluoroethylene), poly(2-methyl-1,3-butadiene), poly(cyclohexyl methacrylate), poly(chlorostyrene), poly(4-methyl styrene), poly(vinyl, cyclohexane), polyphenylene, poly-p-phenylvinylidenes, poly(arylene ether), polyisobutylene, poly(2,6-dimethyl-1,4-phenylene ether), poly[1,1-(2-methyl propane)bis-(4-phenyl)carbonate], poly(a-a-a'-a' tetrafluoro-p-xylylene), fluorinated polyimide, poly(ethylene/tetrafluoroethylene), poly(ethylene/chlorotrifluoroethylene), fluorinated ethylene/propylene copolymer, poly(styrene-co-a-methyl styrene), poly(styrene/butadiene), poly(styrene/2,4-dimethylstyrene), CYTOP, poly(propylene-co-1-butene), poly(styrene-co-vinyl toluene), poly(styrene-block-butadiene-block-styrene), poly(styrene-block-isoprene-block-styrene), terpene resin, poly(N-vinylcarbazole), polycarbazole, polytriarylamine, and the like.

Other exemplary optional polymer binders suitable for the semiconductor composition include a polythiophene, poly (vinyl cinnamate), a triarylamine polymer, a polysiloxane, a polypyrrole, a poly-p-phenylene, a poly-p-phenylvinylidene, or mixtures thereof.

The weight ratio of the compound of Formula (I) to the polymer binder may be from about 99:1 to about 1:3, including from about 10:1 to about 1:2, from about 5:1 to about 2:3, or from about 3:2 to about 3:4.

In embodiments, the small molecule compound of Formula (I) or (II) has a band gap of from about 1.5 to about 3.5 eV, including from about 1.8 to about 2.8 eV. This large band gap typically means that the semiconductor has better stability in air, when compared to a pentacene-based semiconductor. In specific embodiments, the semiconductor of Formula (I) or (II) is colorless in the visible region of the electromagnetic spectrum (i.e. from 390 nm to 750 nm). Colorless semiconductors not only provide excellent stability due to their large band gaps, but also offer advantage in transparency for transparent device applications.

The semiconductor composition may further comprise a solvent in which the compound of Formula (I) and the optional polymer binder are soluble. Exemplary solvents used in the solution may include chlorinated solvents such as chlorobenzene, chlorotoluene, dichlorobenzene, dichloroethane, and the like; alcohols and diols such as propanol, butanol, hexanol, hexanediol, etc.; hydrocarbons or aromatic hydrocarbons such as hexane, heptane, toluene, xylene, ethyl benzene, etc.; ketones such as acetone, methyl ethyl ketone, etc.; acetates, such as ethyl acetate; pyridine, tetrahydrofuran, and the like.

In embodiments, the semiconductor composition comprising the compound of Formula (I) and the polymer binder may have a viscosity of from about 1.5 centipoise (cps) to about 100 cps, including from about 2 to about 20 cps.

The semiconducting layer may be formed in an electronic device using conventional processes known in the art. In embodiments, the semiconducting layer is formed using solution depositing techniques. Exemplary solution depositing techniques include spin coating, blade coating, rod coating, dip coating, screen printing, ink jet printing, stamping, stencil printing, screen printing, gravure printing, flexography printing, and the like.

The semiconducting layer formed using the semiconductor composition can be from about 5 nanometers to about 1000 nanometers deep, including from about 20 to about 100 nanometers in depth. In certain configurations, such as the configurations shown in FIGS. 1 and 4, the semiconducting layer completely covers the source and drain electrodes.

The semiconducting layer is predominantly crystalline. The term "predominantly" refers to the layer having a crystallinity of greater than 50%. In embodiments, the semiconducting layer may have a crystallinity of greater than about 80%, or greater than about 90%. The crystallinity of the semiconductor layer can be determined using any suitable method, for example an X-ray diffraction method.

The performance of a TFT can be measured by mobility. The mobility is measured in units of cm$^2$/V·sec; higher mobility is desired. The resulting TFT using the semiconductor composition of the present disclosure may have a field effect mobility of greater than 0.01 cm$^2$/V·sec, including greater than 0.05 cm$^2$/V·sec, greater than 0.1 cm$^2$/V·sec, or greater than 0.5 cm$^2$/V·sec. The TFT of the present disclosure may have a current on/off ratio of at least 10$^5$, including at least 10$^6$. A thin film transistor generally includes a substrate, an optional gate electrode, source electrode, drain electrode, and a dielectric layer in addition to the semiconducting layer.

The substrate may be composed of materials including but not limited to silicon, glass plate, plastic film or sheet. For structurally flexible devices, plastic substrate, such as for example polyester, polycarbonate, polyimide sheets and the like may be preferred. The thickness of the substrate may be from about 10 micrometers to over 10 millimeters with an exemplary thickness being from about 50 to about 100 micrometers, especially for a flexible plastic substrate and from about 0.5 to about 10 millimeters for a rigid substrate such as glass or silicon.

The dielectric layer generally can be an inorganic material film, an organic polymer film, or an organic-inorganic composite film. Examples of inorganic materials suitable as the dielectric layer include silicon oxide, silicon nitride, aluminum oxide, barium titanate, barium zirconium titanate and the like. Examples of suitable organic polymers include polyesters, polycarbonates, poly(vinyl phenol), polyimides, polystyrene, polymethacrylates, polyacrylates, epoxy resin and the like. The thickness of the dielectric layer depends on the dielectric constant of the material used and can be, for example, from about 10 nanometers to about 500 nanometers. The dielectric layer may have a conductivity that is, for example, less than about 10$^{-12}$ Siemens per centimeter (S/cm). The dielectric layer is formed using conventional processes known in the art, including those processes described in forming the gate electrode.

In the present disclosure, the dielectric layer may be surface modified with a surface modifier. The semiconducting layer can be directly contacted with this modified dielectric layer surface. The contact may be complete or partial. This surface modification can also be considered as forming an interfacial layer between the dielectric layer and the semiconducting layer. In particular embodiments, the surface of the dielectric layer has been modified with an organosilane agent of Formula (A):

$$R_m\text{—Si—}(R'')_{4-m} \qquad \text{Formula (A)}$$

wherein R is a hydrocarbon or fluorocarbon containing from 1 to about 20 carbon atoms, R" is halogen or alkoxy; and m is an integer from 1 to 4. Exemplary organosilanes include octyltrichlorosilane (OTS-8) (R=octyl, R"=chloro, m=1), dodecyltrichlorosilane, phenyltrichlorosilane, methyltrimethoxylsilane, phenylmethyldimethoxysilane, phenylmethyldichlorosilane, (3-phenylpropyl) dimethylchlorosilane, (3-phenylpropyl)methyldichlorosilane, phenyltrimethoxysilane, phenethyltrichlorosilane, and the like. In specific embodiments, the R comprises a phenyl group. Other surface modifiers such as polystyrene, polysiloxane, or polysilsesquioxane can be used as well.

The gate electrode is composed of an electrically conductive material. It can be a thin metal film, a conducting polymer film, a conducting film made from conducting ink or paste, or the substrate itself, for example heavily doped silicon. Examples of gate electrode materials include but are not restricted to aluminum, gold, silver, chromium, indium tin oxide, conductive polymers such as polystyrene sulfonate-doped poly(3,4-ethylenedioxythiophene) (PSS-PEDOT), and conducting ink/paste comprised of carbon black/graphite. The gate electrode can be prepared by vacuum evaporation, sputtering of metals or conductive metal oxides, conventional lithography and etching, chemical vapor deposition, spin coating, casting or printing, or other deposition processes. The thickness of the gate electrode ranges for example from about 10 to about 200 nanometers for metal films and from about 1 to about 10 micrometers for conductive polymers. Typical materials suitable for use as source and drain electrodes include those of the gate electrode materials such as aluminum, gold, silver, chromium, zinc, indium, conductive metal oxides such as zinc-gallium oxide, indium tin oxide, indium-antimony oxide, conducting polymers and conducting inks. Typical thicknesses of source and drain electrodes are, for example, from about 40 nanometers to about 1 micrometer, including more specific thicknesses of from about 100 to about 400 nanometers.

Typical materials suitable for use as source and drain electrodes include those of the gate electrode materials such as gold, silver, nickel, aluminum, platinum, conducting polymers, and conducting inks. In specific embodiments, the electrode materials provide low contact resistance to the semiconductor. Typical thicknesses are about, for example, from about 40 nanometers to about 1 micrometer with a more specific thickness being about 100 to about 400 nanometers. The OTFT devices of the present disclosure contain a semiconductor channel. The semiconductor channel width may be, for example, from about 5 micrometers to about 5 millimeters with a specific channel width being about 100 micrometers to about 1 millimeter. The semiconductor channel length may be, for example, from about 1 micrometer to about 1 millimeter with a more specific channel length being from about 5 micrometers to about 100 micrometers.

The source electrode is grounded and a bias voltage of, for example, about 0 volt to about 80 volts is applied to the drain electrode to collect the charge carriers transported across the semiconductor channel when a voltage of, for example, about +10 volts to about −80 volts is applied to the gate electrode. The electrodes may be formed or deposited using conventional processes known in the art.

If desired, a barrier layer may also be deposited on top of the TFT to protect it from environmental conditions, such as light, oxygen and moisture, etc. which can degrade its electrical properties. Such barrier layers are known in the art and may simply consist of polymers.

The various components of the OTFT may be deposited upon the substrate in any order. Generally, however, the gate electrode and the semiconducting layer should both be in contact with the gate dielectric layer. In addition, the source and drain electrodes should both be in contact with the semiconducting layer. The phrase "in any order" includes sequential and simultaneous formation. For example, the source electrode and the drain electrode can be formed simultaneously or sequentially. The term "on" or "upon" the substrate refers to the various layers and components with reference to the substrate as being the bottom or support for the layers and components which are on top of it. In other words, all of the components are on the substrate, even though they do not all directly contact the substrate. For example, both the dielectric layer and the semiconducting layer are on the substrate, even though one layer is closer to the substrate than the other layer. The resulting TFT has good mobility and good current on/off ratio.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

The invention claimed is:

1. A compound of Formula (I):

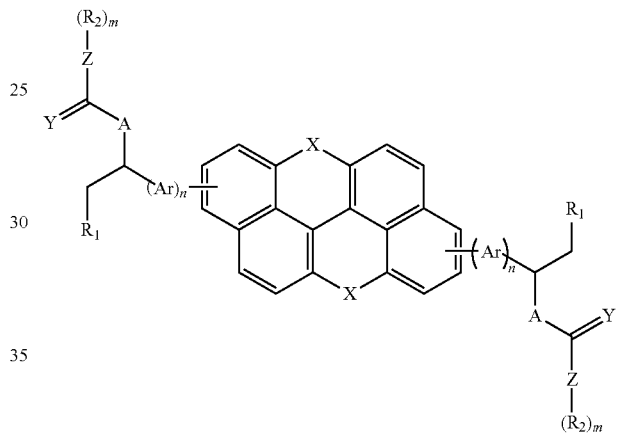

Formula (I)

wherein X is O, S, or N—$R_3$; A is O or S; Y is O or S; Z is O, S, N, or C; each Ar is independently aryl, substituted aryl, heteroaryl, or substituted heteroaryl; each n is independently from 0 to about 2; m is the number of $R_2$ sidechains and is an integer from 1 to 3; $R_1$ and $R_3$ are independently hydrogen, alkyl, substituted alkyl, aryl, heteroaryl, substituted aryl, substituted heteroaryl, alkoxy, alkylthio, alkenyl, substituted alkenyl, alkynyl, substituted alkynyl, trialkylsilyl, arylalkyl, alkylaryl, or halogen; and each $R_2$ is independently hydrogen, alkyl, substituted alkyl, aryl, or substituted aryl.

2. The compound of claim 1, wherein X is oxygen; and $R_1$ is hydrogen, aryl, or heteroaryl.

3. The compound of claim 1, wherein X, A, and Y are O; Z is nitrogen; $R_1$ is hydrogen, phenyl, or thienyl; m is 2; and each $R_2$ is independently hydrogen, alkyl, or substituted alkyl.

4. The compound of claim 1, wherein X, A, and Y are O; Z is carbon; $R_1$ is hydrogen, phenyl, or thienyl; m is 3; and each $R_2$ is independently hydrogen, alkyl, or substituted alkyl.

5. The compound of claim 1, wherein each n is 1; Ar is thienyl or phenyl; $R_2$ is alkyl having from 1 to about 10 carbon atoms, and $R_3$ is alkyl or arylalkyl.

6. The compound of claim 1, wherein X, A, Z, and Y are O; $R_1$ is hydrogen, phenyl, or thienyl; m is 1; and $R_2$ is alkyl or substituted alkyl.

7. The compound of claim 1, wherein the compound has the structure of one of Formula (1) to Formula (16):

Formula (1)
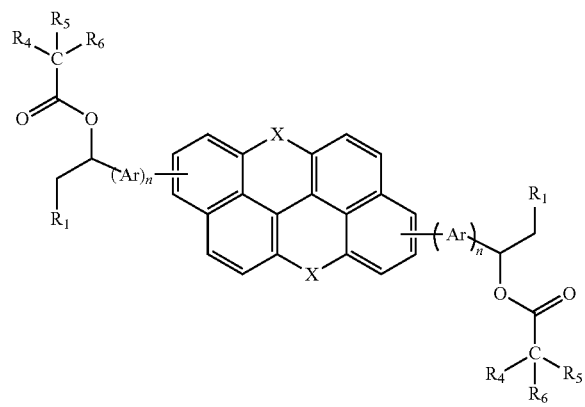
Formula (2)
Formula (3)
Formula (4)
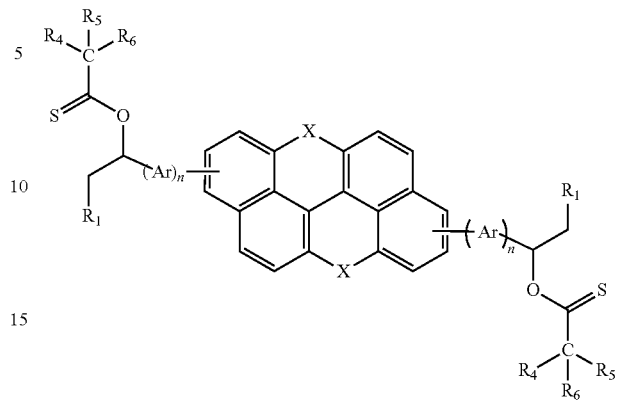
Formula (5)
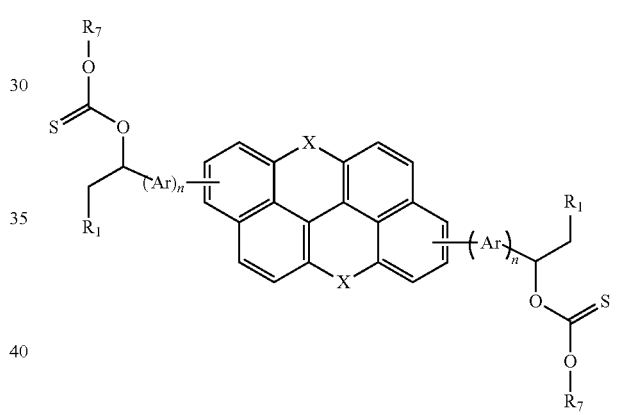
Formula (6)
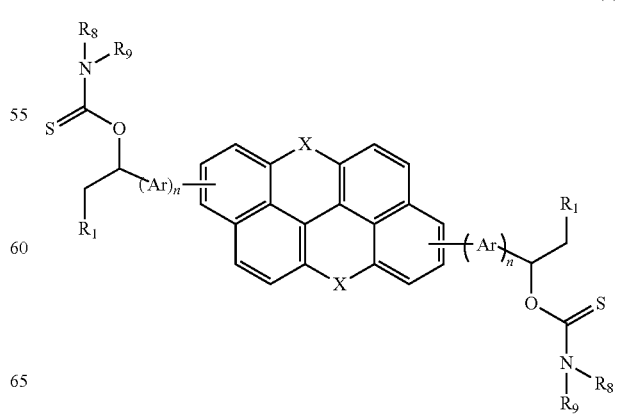

Formula (7)
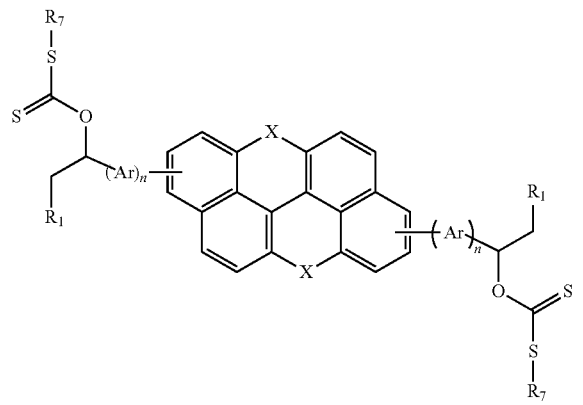
Formula (8)
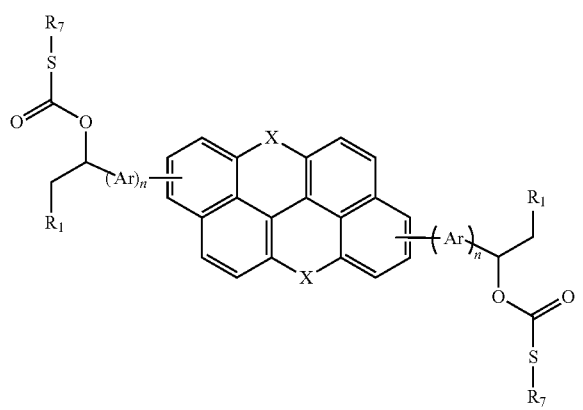
Formula (9)
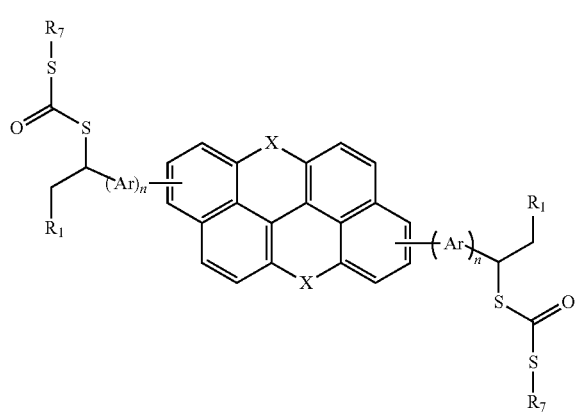
Formula (10)
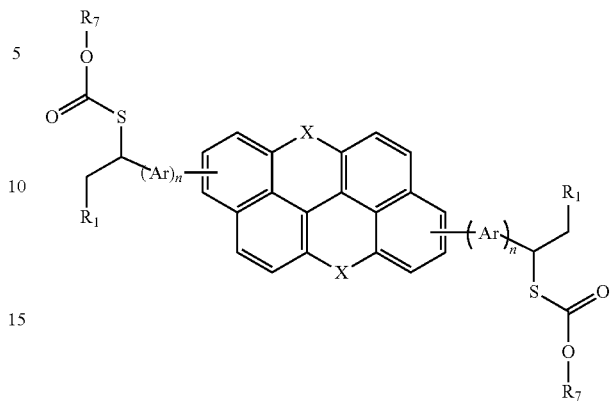
Formula (11)
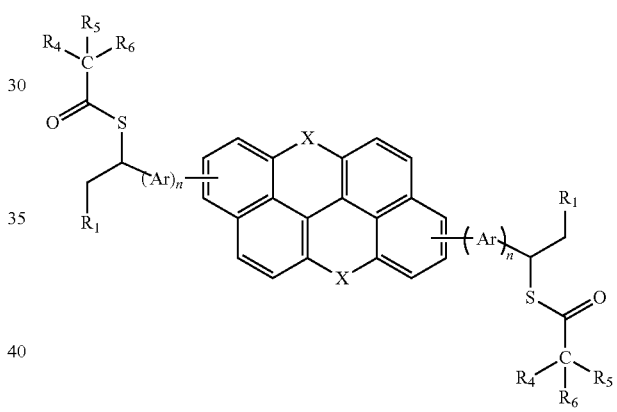
Formula (12)
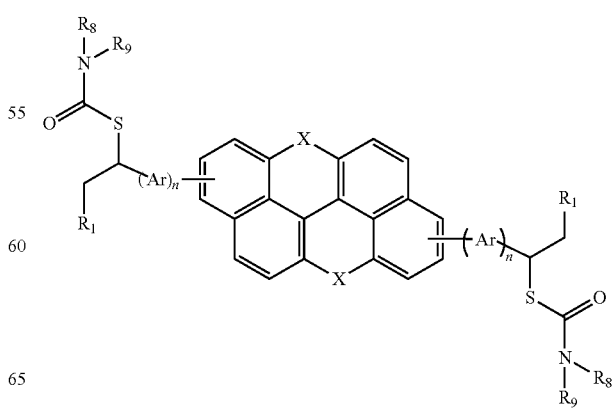

33
-continued (Formula 13)

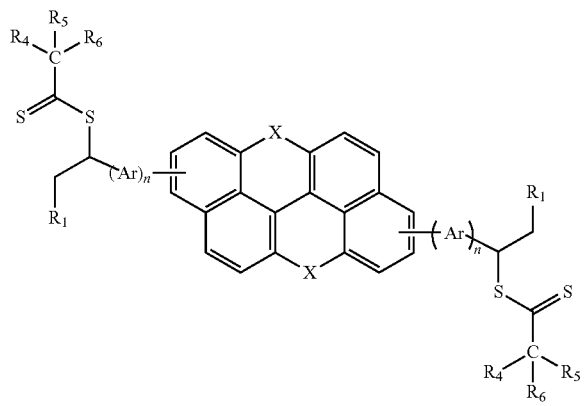

(Formula 14)

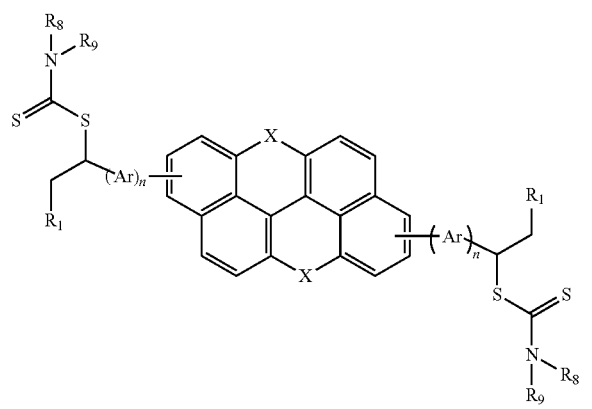

(Formula 15)

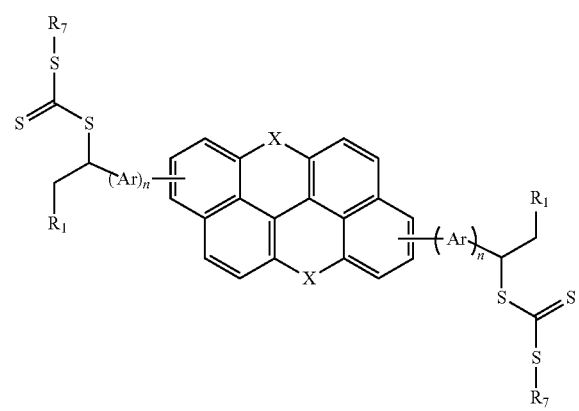

34
-continued (Formula 16)

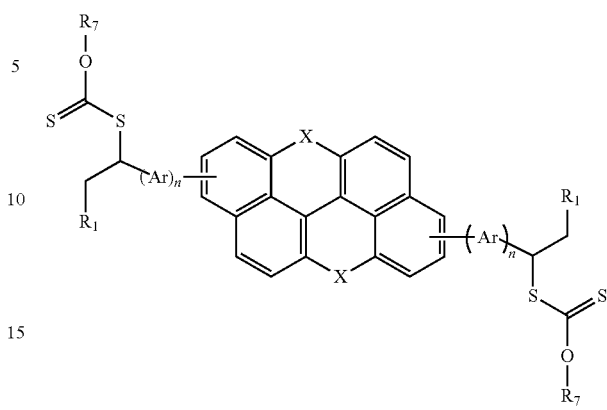

wherein $R_4$, $R_5$, $R_6$, $R_8$, and $R_9$ are independently hydrogen, alkyl, substituted alkyl, aryl, or substituted aryl; and $R_7$ is alkyl, substituted alkyl, aryl, or substituted aryl.

8. A process of fabricating a semiconducting layer of an electronic device, the process comprising:
liquid depositing a semiconductor composition onto a surface; and
heating the semiconductor composition to form a semiconducting layer;
wherein the semiconductor composition comprises a compound of Formula (I):

Formula (I)

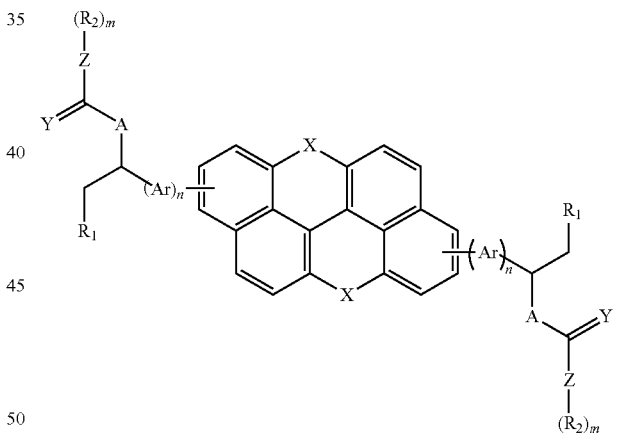

wherein X is O, S, or N—$R_3$; A is O or S; Y is O or S; Z is O, S, N, or C; each Ar is independently aryl, substituted aryl, heteroaryl, or substituted heteroaryl; each n is independently from 0 to about 2; m is the number of $R_2$ sidechains and is an integer from 1 to 3; $R_1$ and $R_3$ are independently hydrogen, alkyl, substituted alkyl, aryl, heteroaryl, substituted aryl, substituted heteroaryl, alkoxy, alkylthio, alkenyl, substituted alkenyl, alkynyl, substituted alkynyl, trialkylsilyl, arylalkyl, alkylaryl, or halogen; and each $R_2$ is independently hydrogen, alkyl, substituted alkyl, aryl, or substituted aryl.

9. The process of claim 8, wherein the semiconductor composition is heated to a temperature of from about 100° C. to about 250° C.

10. The process of claim 8, wherein X is O; and $R_1$ is hydrogen, aryl, or heteroaryl.

11. The process of claim 8, wherein X is O; $R_1$ is hydrogen or aryl; each n is 1; Ar is thienyl or phenyl; and each $R_2$ is hydrogen or alkyl having from 1 to about 10 carbon atoms.

12. The process of claim 8, wherein X, A, and Y are O; Z is carbon; $R_1$ is hydrogen or aryl; m is 3; and each $R_2$ is independently hydrogen, alkyl or substituted alkyl.

13. The process of claim 8, wherein X, A, Y and Z are O; each n is 0; $R_1$ is hydrogen or aryl; m is 1; and $R_2$ is alkyl or substituted alkyl.

14. The process of claim 8, wherein the compound of Formula (I) is an amorphous compound; and the semiconductor layer is predominantly crystalline.

15. An electronic device comprising a semiconducting layer, wherein the semiconducting layer is formed by:
    liquid depositing a semiconductor composition onto a surface; and
    heating the semiconductor composition to form the semiconducting layer;
    wherein the semiconductor composition comprises a compound of Formula (I):

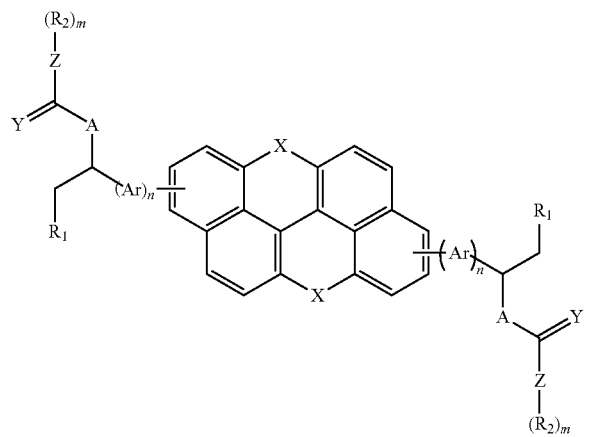

Formula (I)

wherein X is O, S, or N—$R_3$; A is O or S; Y is O or S; Z is O, S, N, or C; each Ar is independently aryl, substituted aryl, heteroaryl, or substituted heteroaryl; each n is independently from 0 to about 2; m is the number of $R_2$ sidechains and is an integer from 1 to 3; $R_1$ and $R_3$ are independently hydrogen, alkyl, substituted alkyl, aryl, heteroaryl, substituted aryl, substituted heteroaryl, alkoxy, alkylthio, alkenyl, substituted alkenyl, alkynyl, substituted alkynyl, trialkylsilyl, arylalkyl, alkylaryl, or halogen; and each $R_2$ is independently hydrogen, alkyl, substituted alkyl, aryl, or substituted aryl.

16. The electronic device of claim 15, wherein $R_1$ is hydrogen, aryl, or heteroaryl.

17. The electronic device of claim 15, wherein each n is 0.

18. The electronic device of claim 15, wherein X, A and Y are O; Z is carbon, $R_1$ is hydrogen, phenyl, or thienyl; m is 3; and each $R_2$ is independently hydrogen, alkyl or substituted alkyl.

19. The electronic device of claim 15, wherein the semiconductor layer is predominantly crystalline.

20. The electronic device of claim 15, wherein the semiconductor layer comprises a compound of Formula (II) and a residual amount of the compound of Formula (I):

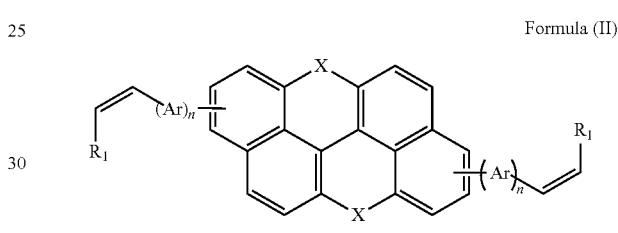

Formula (II)

wherein X is O, S, or N—$R_3$; each Ar is independently aryl, substituted aryl, heteroaryl, or substituted heteroaryl; each n is independently from 0 to about 2; and $R_1$ is hydrogen, alkyl, substituted alkyl, aryl, heteroaryl, substituted aryl, substituted heteroaryl, alkoxy, alkylthio, alkenyl, substituted alkenyl, alkynyl, substituted alkynyl, trialkylsilyl, arylalkyl, alkylaryl, or halogen.

* * * * *